United States Patent [19]

Greco

[11] 4,431,848

[45] Feb. 14, 1984

[54] PREPARATION OF RESORCINOL AND SUBSTITUTED RESORCINOLS BY LIQUID-PHASE DEHYDROGENATION OF 1,3-CYCLIC DIONES DERIVED BY VAPOR-PHASE CYCLIZATION OF DELTA-KETO CARBOXYLIC ACID ESTERS

[75] Inventor: Nicholas P. Greco, Edgewood, Pa.

[73] Assignee: Koppers Company, Inc., Pittsburgh, Pa.

[21] Appl. No.: 372,030

[22] Filed: Apr. 26, 1982

[51] Int. Cl.³ .............................................. C07C 37/00
[52] U.S. Cl. ................................................... 568/772
[58] Field of Search ............................... 568/772, 799

[56] References Cited

U.S. PATENT DOCUMENTS

| | | | |
|---|---|---|---|
| 3,824,272 | 7/1974 | Brossi et al. | 568/772 |
| 3,950,438 | 4/1976 | Schaafsma | 568/772 |
| 4,018,833 | 4/1977 | Muller et al. | 568/772 |
| 4,072,660 | 2/1978 | Muller et al. | 568/772 |
| 4,154,965 | 5/1979 | Meijer et al. | 568/772 |
| 4,160,113 | 7/1979 | Muller et al. | 568/772 |
| 4,250,336 | 2/1981 | Muller et al. | 568/772 |

FOREIGN PATENT DOCUMENTS 2411371  9/1974  Fed. Rep. of Germany ...... 568/772

*Primary Examiner*—Werren B. Lone
*Attorney, Agent, or Firm*—Donald M. MacKay; J. Timothy Keane; Herbert J. Zeh, Jr.

[57] ABSTRACT

A process is disclosed for making resorcinol and substituted resorcinols by a first reaction step of vapor-phase cyclization of a delta-keto carboxylic acid ester over a carbon catalyst bed to form a 1,3-cyclic dione intermediate. The delta-keto ester is conveyed through the catalyst bed by a vaporized carrier characterized by being liquid at 25° C. and having a sufficiently high boiling point that the vaporized carrier is easily condensable under ambient conditions. In a second reaction step, a liquid solvent containing the 1,3-cyclic dione intermediate is contacted with a supported noble-metal catalyst to form resorcinol or a substituted resorcinol.

17 Claims, No Drawings

PREPARATION OF RESORCINOL AND SUBSTITUTED RESORCINOLS BY LIQUID-PHASE DEHYDROGENATION OF 1,3-CYCLIC DIONES DERIVED BY VAPOR-PHASE CYCLIZATION OF DELTA-KETO CARBOXYLIC ACID ESTERS

BACKGROUND OF THE INVENTION

1. Field of the Invention

Preparation of resorcinol and substituted resorcinols by catalytic dehydrogenation of certain 1,3-cyclic diones is well known. Of particular interest herein are process improvements in the preparation of resorcinol and substituted resorcinols made by dehydrogenation of 1,3-cyclic diones derived by the vapor-phase cyclization of delta-keto carboxylic acid esters.

2. State of the Art

U.S. Pat. No. 4,072,660 to Muller et al. describes the preparation of resorcinol and substituted resorcinols by cyclization of 4-oxocarboxylic acid esters to cyclohexane-1,3-dione type intermediates, followed by dehydrogenation of the intermediates to the corresponding resorcinol or substituted resorcinols. The cyclohexane-1,3-dione intermediate is prepared by a first-step liquid-phase cyclization of a 4-oxocarboxylic acid alkyl ester or a delta-enollactone in a glycol ether solvent in the presence of a stoichiometric amount of a strong base such as sodium methylate to provide a sodium salt of the cyclohexanedione, and a second step of acidification of the sodium salt to form the cyclohexanedione intermediate. Dehydrogenation of the intermediate is accomplished in the same glycol ether solvent in the presence of a supported noble metal catalyst, such as a palladium-on-carbon catalyst. The Muller '660 preparation has the disadvantages of requiring an expensive solvent for the liquid-phase preparation of the cyclohexanedione intermediate, and of requiring a strong alkali catalyst for the cyclization step followed by the need for a strong acid to spring the cyclohexanedione from the alkali salt of the cyclization product. Residual mineral acid from the cyclohexanedione springing step can inhibit the activity of the noble metal catalyst during the dehydrogenation step. Moreover, the Muller '660 preparation generates significant quantities of effluent, the recovery and disposal of which is costly.

In U.S. Pat. No. 4,250,336 to Muller et al., cyclization of a delta-ketocarboxylic acid ester and dehydrogenation of the cyclohexane-1,3-dione to the corresponding resorcinol or substituted resorcinol are accomplished in a one-step gas phase reaction in the presence of hydrogen/nitrogen carrier and a catalyst. The catalyst is typically provided by a two-component mixture of thorium-on-carbon and platinum/chrome oxide-on-alumina. This one-step process is disadvantageous inasmuch as the reaction product contains substantial amounts of various by-products and residual delta-ketocarboxylic acid ester starting material. It is difficult to separate commercially-useable resorcinol or substituted resorcinol from the Muller '336 reaction product mixture, and especially from the delta-ketocarboxylic acid ester starting material and the cyclohexane-1,3-dione intermediate in the reaction product mixture. Moreover, the process requires an expensive catalyst which, once deactivated by use in the one-step cyclization-dehydrogenation reaction, cannot practically be reactivated to the previous degree of activation.

In U.S. Pat. No. 4,160,113 to Muller et al, resorcinol and substituted resorcinols are prepared by catalytic dehydrogenation of cyclohexane-1,3-diones in a liquid phase. The liquid phase is provided by a large variety of dehydrogenation solvents having a wide range of boiling points. Where low-boiling solvents are used, i.e., boiling points below about 160° C., the reaction must be under pressure in order to utilize optimum dehydrogenation temperatures. Thus, a preferred class of dehydrogenation solvents is provided by glycol ethers having boiling points in a range from about 180° C. to about 260° C. Use of many of these Muller '113 high-boiling solvents for dehydrogenation media is disadvantageous inasmuch as the solvent, the resorcinols and other phenolic by-products may have boiling points so similar that separation of desired product from by-products and from the solvent is very difficult.

There remains need, therefore, for a process for making resorcinol or substituted resorcinol in high yields with relatively low amounts of easily separable by-products.

SUMMARY OF THE INVENTION

A process is provided for making resorcinol or substituted resorcinol of the general formula

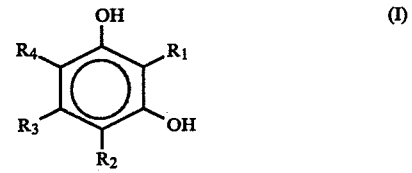

wherein $R_1$ through $R_4$ are selected from hydrogen and alkyl groups of about six carbon atoms, with the proviso that the total number of carbon atoms of $R_1$ through $R_4$ cannot exceed about 24. The process comprises a first-step vapor-phase catalytic cyclization of a delta-ketocarboxylic acid ester to a cylic dione intermediate and a second-step liquid-phase dehydrogenation of the cyclic dione intermediate to resorcinol or a substituted resorcinol as defined by formula I. The first step of the process comprises passing a vapor stream through a reaction zone containing a carbon catalyst. The vapor stream comprises a delta-ketocarboxylic acid ester mixed with or dissolved in an easily-condensable non-reactive carrier. The term "delta-keto ester" as used herein is an abbreviated expression for the term "delta-ketocarboxylic acid ester" and embraces compounds defined by the general formula

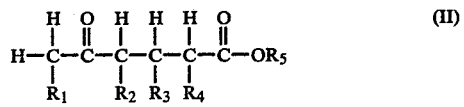

wherein $R_1$ through $R_4$ are as defined for general formula I and $R_5$ is selected from alkyl, aryl and alkylaryl groups, with the proviso that the total number of carbon atoms of $R_5$ cannot exceed about 24. The non-reactive carrier is selected such that the delta-keto ester starting material is soluble in the carrier. Also, it is preferred that the carrier be selected such that the cyclic dione intermediate is only slightly soluble or insoluble in the carrier, or be selected such that the cyclic dione intermediate is only slightly soluble or insoluble in the selected carrier in combination with unreacted starting ester and alcohol by-products formed during the cyclization reaction. Moreover, a suitable carrier must be liquid at 25° C. under one atmosphere and must have a sufficiently high boiling point that it is condensable from the gas phase at about 25° C. under ambient atmospheric conditions.

The vapor stream leaving the reaction zone, containing the cyclic dione intermediate together with some unreacted delta-keto ester starting material and an alcohol formed as a by-product in the cyclization reaction, is then condensed. Condensing the vapor stream to a liquid is accomplished with conventional water-cooled equipment inasmuch as an easily-condensable carrier is utilized.

The second step of the process comprises contacting a liquid solution containing cyclic dione obtained in the first step with a supported noble metal catalyst. The second step is conducted under conditions of reaction time, pressure and temperature effective to dehydrogenate the cyclic dione so as to form resorcinol or a substituted resorcinol.

An advantage of the first step of the process resides in use of a vapor-phase reaction medium in which the carrier gas is easily condensable into a liquid as compared to carrier gases utilized heretofore. In prior processes, carrier gases such as hydrogen and nitrogen are utilized in a gas stream having relatively high carrier-to-ester ratios and traveling at high velocity; separation of vaporized products and contaminants from such carrier gases requires cooling of the gas stream to −20° C. or less to allow separation of products from the gas stream. This cooling step must be provided at relatively high cost in terms of refrigeration and condensing equipment and energy requirements. The use of an easily condensable carrier as provided in the present process obviates the need for a relatively expensive gas condensing step.

An advantage of the second step of the process is in providing a dehydrogenated reaction product containing relatively low amounts of by-products which are easily separable from the desired resorcinol or substituted resorcinol by simple distillation techniques. Hence, in combination the two steps of the process of the invention provide a high yield of product without formation of troublesome contaminants or by-products.

The process of the invention is particularly suitable for preparing resorcinol, that is, 1,3-dihydroxybenzene, by a first step of cyclization of methyl 4-oxocaproate to 3-hydroxy-2-cyclohexene-1-one intermediate, followed by a second step of dehydrogenation of this intermediate to resorcinol.

DETAILED DESCRIPTION OF THE INVENTION

Vapor-phase cyclization of delta-keto ester in the first step of the process produces cyclic dione intermediate which may be tautomeric in character and thus may be expressed by either or both of the following structures

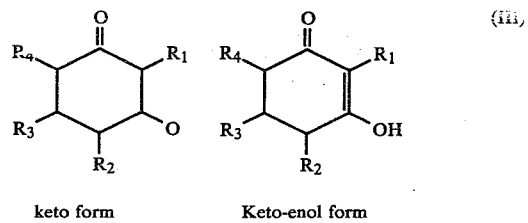

keto form      Keto-enol form wherein $R_1$ through $R_4$ are as defined above for general formula I. Whether a particular cyclic dione is in the diketo form or the Keto-enol form will usually depend upon the nature of the "R" substituents and the properties of the medium in which the cyclic dione is dissolved, such as solvent type, temperature, pressure and pH. As used herein, the term "cyclic dione" is intended to embrace an intermediate formed by the first-step cyclization of a delta-keto ester. Such intermediate may be variously called "1,3-cyclic dione", "cyclohexanedione", "cyclohexane-1,3-dione", "substituted 1,3-cyclic dione", "substituted cyclohexanedione", and "substituted cyclohexane-1,3-dione". An intermediate of particular interest as a precursor to resorcinol is formed by cyclization of methyl 4-oxocaproate. This intermediate when isolated as a crystalline material exists in the Keto-enol form and is identified as follows:

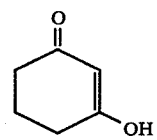 (IV)

3-hydroxy-2-cyclohexene-1-one

The intermediate of formula IV, also known as "dihydroresorcinol" or "DHR", may be dehydrogenated in accordance with the second step of the process of the invention to form resorcinol.

Starting materials for use in the first step of the present process comprise delta-ketocarboxylic acid esters having the general formula II, above, in which the $R_1$ through $R_4$ substituents may be selected from hydrogen and lower alkyl groups; preferred substituents are methyl, ethyl and propyl groups. The $R_5$ substituent may be provided by various alkyl groups, whether linear, branched or cyclic, by various aryl groups, whether mononuclear, binuclear or polynuclear, and by various mono- or polynuclear alkylaryl groups. Preferred alkyl groups for the $R_5$ substituent include methyl, ethyl, n-propyl, isopropyl, n-butyl, sec-butyl and n-hexyl groups. Typical aryl groups include phenyl and naphthyl groups. A typical alkylaryl group is benzyl. As used herein, the term "delta-keto carboxylic acid ester" is synonomous with "5-oxohexanoic acid ester", "delta-keto ester", "delta-keto acid ester" and "alkanoic carboxylic acid ester", all of which terms describe monocarboxylic acids derived from linear alkanes.

Esters which may be used as starting materials in the process are 5-oxohexanoic acid esters prepared generally by the reaction of an acrylic acid ester with a suitable alkyl- or aryl-substituted ketone. Useful acrylic acid esters are those having the general formula

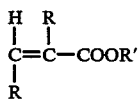

wherein R may be hydrogen, or an alkyl, aryl, or alkylaryl group, and R' may be an alkyl, aryl, or alkylaryl group. Examples of suitable acrylic acid esters are methyl acrylate, methyl methacrylate, ethyl acrylate, ethyl methacrylate, butyl acrylate, octyl acrylate and dodecyl acrylate. Suitable ketones are those having one or more labile hydrogens on a carbon in alpha-position to the ketone carbonyl group. Examples of suitable aliphatic ketones are acetone, methyl ethyl ketone, methyl propyl ketone, diethyl ketone, methyl isopropyl ketone, methyl heptyl ketone, acetyl acetone and acetonyl acetone. Examples of suitable cycloaliphatic ketones are cyclopentanone and cyclohexanone. An example of a suitable alkylaryl ketone is benzyl methyl ketone. Conditions for preparation of these 5-oxohexanoic acid esters are found in U.K. Pat. No. 1,473,184.

Specific delta-keto esters which may be useful in the process are methyl 4-oxocaproate (a.k.a. 5-oxohexanoic acid methyl ester), 5oxohexanoic acid n-butyl ester, 5-oxohexanoic acid isopropyl ester, 5-oxohexanoic acid isobutyl ester, 4-methyl-5-oxohexanoic acid methyl ester, 5-oxoheptanoic acid methyl ester, 4-methyl-5-oxoheptanoic acid methyl ester, 4-n-propyl-5-oxohexanoic acid methyl ester, 5-oxononanoic acid methyl ester, 5-oxo-4-phenylhexanoic acid methyl ester, and 5-oxo-6-phenylhexanoic acid methyl ester.

A non-reactive, easily-condensable liquid carrier is used to convey the delta-keto ester into a cyclization reactor. The term "non-reactive" characterizes a carrier which is substantially inert with respect to reaction with the delta-keto ester, to reaction with the cyclization product, and to reaction with the catalyst under conditions of cyclization. The term "easily-condensable" characterizes a carrier having a sufficiently high boiling point that the carrier changes from the vapor state to a liquid under ambient conditions, namely, at about one atmosphere pressure and at about 25° C. It is preferred that the delta-keto ester and the carrier be selected for use in the cyclization process so that delta-keto ester is soluble in the carrier, but so the cyclization product is only slightly soluble, or much less soluble than the ester, in the carrier. The carrier may be provided by a single compound or by a multi-component mixture.

Materials suitable as single-compound carriers are liquid at about 25° C. under one atmosphere pressure and may be selected from the following general classes of compounds: organic acids, hydrocarbons and aliphatic hydrocarbons. Examples of suitable organic acids are acetic acid, propionic acid and pelargonic acid. Examples of aromatic hydrocarbons are benzene, toluene, o-, m-, p-xylenes, cumene, pseudocumene, ethylbenzene, isodurene and prehnitene. Examples of aliphatic hydrocarbons are alkanes of six to ten carbon atoms.

Particularly suitable for use as a carrier in the first-step cyclization of the process for the manufacture of resorcinol is a vapor carrier provided by a multi-component system, that is, the carrier may be provided by a mixture of two or more miscible components. At least one of these components is an aliphatic hydrocarbon and at least one component is an aromatic hydrocarbon.

The aliphatic hydrocarbon is selected from aliphatic hydrocarbons which are liquid at room temperature and which have normal boiling points greater than about 50° C., to satisfy the requirement of the invention that the carrier be easily condensable at room temperature. Also, the selected aliphatic hydrocarbon must be capable of forming an azeotropic mixture with by-product alcohol produced during the cyclization reaction. In the preparation of resorcinol, the by-product alcohol is methanol; thus the selected aliphatic hydrocarbon must be capable of forming an azeotrope with methanol. An aliphatic hydrocarbon which satisfies all of these criteria as a carrier component in the preparation of cyclization product as a precursor to resorcinol is n-hexane. Other aliphatic hydrocarbons may be used in combination with n-hexane, such as n-heptane, isohexanes and isoheptanes. The aromatic hydrocarbon component may be any easily-condensable compound such as listed above in the examples of aromatic hydrocarbons of the single-compound carriers. In the preparation of resorcinol precursor, the aromatic hydrocarbon component is toluene.

In preparation of resorcinol by a first-step cyclization of methyl 4-oxocaproate (MOC) conveyed through the catalyst bed by the multi-component carrier comprising n-hexane as the aliphatic component and toluene as the aromatic component, the mole ratio of MOC/n-hexane/toluene may be in a range of about one/three/one to about one/ten/one; a mole ratio of one/five/one is preferred.

A reactor suitable for the cyclization reaction is typically a fixed-bed type reactor having a preheater or vaporization zone and a catalysis or reaction zone. The preheater or vaporization zone may be provided by a bed of Pyrex glass beads or similar material capable of being heated and held to a temperature of about 500° C. Adjacent to the vaporization zone is a reaction zone containing a catalyst in a fixed bed mode. The catalyst is a carbon material capable of catalyzing the cyclization of a delta-keto ester to cyclic dione intermediate. The carbon catalyst is usually comprised of particles having diameters in a range from about 0.4 mm to about 1.0 mm, having specific surface area in a range from about 900 m$^2$/g to about 1400 m$^2$/g, and having a pore volume in a range from about 0.8 cc/g to about 1 cc/g. The catalyst bed is typically packed with carbon to a density in a range from about 20 lbs/ft$^3$ to about 40 lbs/ft$^3$. Useful carbon catalysts include Filtrasorb No. 300 and No. 400 series carbon catalysts sold by Calgon Corp., Pittsburgh, PA, and Nuchar series 503 and WV-H activated carbon catalysts sold by Westvaco, Covington, Va. These catalysts are used as purchased without any modification as to composition. These catalysts are characterized in being devoid of Group IIIB and Group IVB elements of the Periodic System. Before introduction of the delta-keto ester and carrier into the reactor, the preheater bed and the catalyst bed are heated to about 400° C. Then hydrogen is passed through the reactor for a period of time, typically about 16 hours, in order to activate the catalyst bed.

The delta-keto ester starting material is dissolved in the liquid carrier to form a solution such that the ester is present in the solution in an amount in a range from about 8 to about 26 mole percent of the liquid solution. A liquid stream containing the carrier and ester is then introduced to the reactor preheater bed usually held at a temperature in a range from 300° C. to about 500° C.

in order to vaporize the carrier and ester into a gaseous stream. Rate of delivery of the liquid stream generally depends upon the dimensions of the reactor. The vapor stream enters the activated carbon catalyst bed of the reaction zone under pressure as furnished by the back pressure from the vaporization of the liquid stream in the preheater section. Typically, the temperature of the carbon catalyst bed is held substantially uniformly throughout the bed length in a range from about 300° C. to about 400° C. The vapor stream travels through the carbon bed at a liquid hourly space velocity in a range from about 0.13 to about 0.21, with a catalyst contact time in a range from about three seconds to about eight seconds.

After leaving the catalysis zone of the reactor, the vapor stream enters a condensing zone which is maintained typically at a temperature in a range from about 20° C. to about 50° C. More usually, the condensing zone is maintained at ambient temperature and atmospheric conditions, namely, at about 25° C. and one atmosphere pressure. It is an advantage of the process of the invention that complicated and expensive refrigeration and condensing equipment are not rquired for removal of cyclization reaction products from the vapor stream. Thus, a simple collecting vessel remote from the heated reactor may be used for condensing the vapor stream and receiving the resulting liquid. It is preferred that a carrier be selected such that the delta-keto ester starting material is freely soluble in the carrier while the cyclic dione product is only slightly soluble, or substantially insoluble, in the carrier. After the condensing step, isolating the cyclic dione may be accomplished by precipitation or crystallization of the cyclic dione from the condensed carrier, while unreacted delta-keto ester will desirably remain dissolved in the liquid carrier. In separation of some cyclic diones from the condensed liquid stream, the carrier material is removed from the liquid stream by distillation at reduced pressure, thereby leaving cyclic dione product mixed with or dissolved in unreacted delta-keto ester. Precipitated or crystallized cyclic dione product may then be filtered from the liquid carrier or from unreacted delta-keto ester, as the case may be, and washed with a solvent, typically the same solvent as used for the carrier, and then dried to provide relatively pure cyclic dione product in high yield.

In preparation of resorcinol involving a first-step conveyance of methyl 4-oxocaproate through the catalyst bed by use of the multi-component n-hexane/toluene carrier, it has been found that the resorcinol precursor or intermediate 3-hydroxy-2-cyclohexene-1-one has very low solubility in the condensed liquid two-component carrier. Hence, separation of this cyclic dione intermediate from unreacted methyl 4-oxocaproate and from the carrier is substantially complete without the use of complicated or expensive distillation or fractionation steps.

Unreacted delta-keto ester may be recycled continuously into a fresh liquid stream introduced to the cyclization reactor. It has been found that a continuous vapor-phase cyclization process in accordance with the invention is capable of an ultimate yield of cyclic dione product of 100 percent. "Ultimate yield" is defined as per-pass yield of cyclic dione product divided by conversion of delta-keto ester starting material.

For the second step of the process, the "dehydrogenation step", cyclic dione crystals isolated from the first step are dissolved in a selected dehydrogenation solvent. The term "dehydrogenation solvent" is intended to embrace four types of solvents useful as reaction media for dehydrogenation of the cyclic dione, provided that a selected solvent has a normal boiling point of less than about 170° C. The four types of solvents are aliphatic alcohols of two to about seven carbon atoms, esters of aliphatic acids, aliphatic ethers and water. Mixtures of two or more of these solvents selected from the same or different types may also be used as dehydrogenation media provided that the solvents selected are mutually miscible.

Suitable aliphatic alcohols as dehydrogenation solvents include ethyl, propyl, isopropyl, butyl, amyl, hexyl and heptyl alcohols. Suitable esters as solvents include aliphatic esters such as ethyl acetate, propyl acetate, butyl acetate, isobutyl acetate, amyl acetate and neopentyl acetate. Suitable aliphatic ethers include dibutyl ether, methyl hexyl ether, methyl pentyl ether and dioxane.

Of these dehydrogenation media aliphatic esters are preferred, with acetate esters more preferred; butyl acetate is an especially preferred dehydrogenation solvent.

The dehydrogenation step is usually performed in a stainless steel pressure reactor equipped with stirring means, a starting material feed line, a reaction product outlet line and a nitrogen purge feed line. For a continuous reaction, an amount of starting material feed is prepared in advance of the reaction. Cyclic dione crystals obtained from the first step of the invention are dissolved in a selected dehydrogenation solvent in an amount typically of about ten weight percent dione-in-solvent. The reactor is charged with a solvent identical to the solvent used to prepare the starting material feed. Then a supported noble metal catalyst is charged to the reactor. Typically useful noble metals are platinum, palladium and rhodium; palladium is preferred. Useful supports include powdered carbon, alumina, silica, calcium carbonate and barium sulfate. The catalyst usually has from about 0.5 to about 10 weight percent of noble metal on the support. Catalyst having about 5 weight percent noble metal on the support is preferred. An amount of catalyst is charged to the reactor depending upon the total amount of dehydrogenated cyclic dione product produced over a continuous run. Typically, for a 5 weight percent palladium-on-carbon catalyst, 100 parts of cyclic dione are produced by use of 4 parts of the catalyst.

The dehydrogenation reaction is run typically under reflux conditions and with stirring of the dehydrogenation solvent sufficient to maintain the catalyst suspended and dispersed uniformly throughout the solvent. Cyclic dione feed may be introduced at a concentration in a range from about 5 to about 30 weight percent dione-in-feed solvent. At high feed concentration, e.g., 25 weight percent, the feed must be maintained at a temperature of about 80° C. as it is added to the reactor. Usually, the dehydrogenation solvent is maintained at a temperature in a range from about 170° C. to about 250° C. For dehydrogenation of dihydroresorcinol to resorcinol, the dehydrogenation solvent is maintained at a temperature in a range from about 170° C. to about 200° C. During reaction, pressure is maintained above the surface of the dehydrogenation solvent by means of a nitrogen gas purging stream introduced below the surface of the solvent. The pressure is usually maintained in a range from about one atmosphere to about 20 atmospheres depending upon the vapor pressure of the dehydrogenation solvent selected and the temperature at which the dehydrogenation reaction occurs. The nitrogen gas stream also purges hydrogen from the reaction mixture as it is generated during the dehydrogenation reaction.

As the reaction proceeds, both hydrogen and dehydrogenated product are removed from the reaction mixture at about the same rate that the cyclic dione feed stream is introduced to the reactor. A filter positioned in the product discharge line prevents suspended catalyst from leaving the reactor. Usually, cyclic dione feed rate is adjusted to provide a two-to-six hour residence time in the reactor. Highest yields of resorcinol, for example, are obtained with a three-to-four hour residence time. Residence times longer than about four hours usually result in higher phenol by-product. Residence times less than about three hours provide less phenol by-product but more distillation residue, typically being trihydroxydiphenyl. Within the aforementioned temperature and pressure reaction parameters, a reaction temperature may be selected which is most suitable for a particular pressure established by the nitrogen blanket.

The following examples set forth specific embodiments of the invention. The invention is not to be construed, however, as being limited to these embodiments for there are, of course, numerous possible variations and modifications. All parts and percentages of the examples as well as throughout the specification are by weight unless otherwise indicated.

EXAMPLE I

A vertically-oriented Pyrex glass reactor tube 36 inches in length and one inch in diameter was packed with about 44 g of Filtrasorb No. 400 activated carbon (Calgon Corp., Pittsburgh, PA) to make a uniformly-dense catalyst bed about ten inches in length and occupying about 97 cc volume. Resting on top of the carbon catalyst bed was a three-inch thick layer of ⅛-inch diameter Pyrex glass beads, which layer provides a preheater bed. The reactor tube was placed in a furnace constructed to receive the reactor tube in a sleeve fitting such that the furnace heated the catalyst and preheater beds. Located within upper, middle and lower portions of the catalyst bed were temperature sensing thermocouples. In order to activate the catalyst bed, hydrogen gas was passed through the catalyst bed for a period of about 16 hours with the bed temperature maintained at about 400° C.

After the reactor tube reached equilibrium conditions with a temperature maintained at about 375° C. in the preheater and carbon beds, a liquid mixture containing methyl 4-oxocaproate (MOC) and toluene was pumped into the reactor tube over a period of about five hours at a rate of about 28 ml/hr. The liquid mixture contained 0.08 mole MOC for every 0.62 mole toluene (11.4 mole percent ester-in-liquid stream); for each one-hour pumping period, 18.7 g MOC and 53.4 g toluene were delivered into the reactor tube. When the liquid mixture contacted the glass-bead preheater bed, the mixture immediately vaporized and formed a gas having a back pressure of about 0.3 mm Hg, as measured at the preheater bed. With a catalyst bed free space of 150 ml, the reaction mixture had a catalyst contact time of about 5.2 seconds and a liquid hourly space velocity of 0.21. The product vapor stream leaving the reactor tube condensed into a liquid on the unheated portion of the walls of the reactor tube. Condensed liquid was collected in a receiving vessel at room temperature. Gas chromatographic analysis of a sample of condensate collected during the third and fourth hours of the reaction period showed 7.4 wt. % 3-hydroxy-2-cyclohexene-1-one (DHR), 73 wt. % toluene, 17.0 wt. % unreacted MOC, and a small amount of methanol by-product; these products correspond to a conversion of 36 mole percent MOC to DHR. No phenol contaminant by-product was detected in the product stream.

The toluene carrier was removed from the condensate by distillation at 50° C. under reduced pressure. Care was taken to maintain the temperature of the condensate below 90° C. during distillation in order to avoid decomposition of the 3-hydroxy-2-cyclohexene-1-one product. Residue from distillation was allowed to cool to room temperature, at which temperature there formed light yellow crystals in contact with an amber-colored liquid. The crystals were separated from the liquid by filtration; then the crystals were pressed to remove residual MOC and washed with toluene; and thereafter the crystals were dried to remove toluene. Analysis of dried crystals showed 98 wt. % 3-hydroxy-2-cyclohexene-1-one and 2 wt. % MOC, which crystals were suitable for use directly in the conversion of 3-hydroxy-2-cyclohexene-1-one into resorcinol by dehydrogenation.

A cyclic dione feed solution was prepared by dissolving 57 g of the previously-prepared and dried 3-hydroxy-2-cyclohexene-1-one crystals in 515 g of isopropyl alcohol. The resulting solution had a concentration of ten weight percent of the cyclic dione in isopropyl alcohol. For the dehydrogenation reaction, a 500 ml stainless steel pressure reactor was equipped with stirring means, a thermocouple, a water-cooled reflux condenser, a cyclic dione feed line, a nitrogen gas purging line, and a stainless steel frit-filter in series with a product discharge line. To the reactor there was charged 200 ml of isopropyl alcohol, as the dehydrogenation solvent, together with about 5 g of powdered 5 weight percent palladium-on-carbon catalyst (catalyst No. 18-512, Englehart Industries Newark, N.J.). The catalyst and alcohol were heated to a temperature of about 170° C. under agitation so as to disperse the catalyst within the solvent. A nitrogen gas stream for purging hydrogen from the reactor mixture was introduced under the surface of the solvent; a nitrogen blanket established above the solvent was maintained at a pressure of about 175 p.s.i.g. To this pressurized, heated reaction mixture at a point below the surface of the reaction mixture there was introduced the previously-prepared cyclic dione feed stream at a rate of about 50 ml/hr. Over the reaction period, a total of about 715 ml of cyclic dione feed was introduced to the reaction mixture. The volume of the reaction mixture was kept about constant by intermittent removal of the resorcinol reaction product at a rate equal to addition of the cyclic dione feed solution. During the reaction period, the temperature and pressure were maintained at about 175° C. and at about 175 p.s.i.g., respectively. Resorcinol reaction product was collected in a pressure receiver attached to the discharge line. The reaction product was distilled to remove isopropyl alcohol, there being left about 60 g of crude resorcinol residue. The residue was flash distilled without fractionation to provide 57 g of resorcinol which was 92.5 percent pure resorcinol as determined by a freezing point method. Overall conversion of 3-hydroxy-2-cyclohexene-1-one to resorcinol was 95 percent.

EXAMPLE II

A cyclic dione feed solution was prepared by dissolving 16.8 g of 3-hydroxy-2-cyclohexene-1-one crystals, prepared as described in Example I, in 224 g of butyl acetate. To a reactor equipped as in Example I, there was charged 300 ml of butyl acetate, as the dehydrogenation solvent, together with 4 g of 5 weight percent powdered palladium-on-carbon catalyst. The dehydrogenation reaction was run as described in Example I, at a temperature of about 170° C., under a pressure of about 40 p.s.i.g., and with a cyclic dione feed rate of 60 ml/hr over a 4.2 hour reaction period. Crude resorcinol was recovered in an amount of 16.6 g of about 95 percent purity with a conversion of 3-hydroxy-2-cyclohexene-1-one of 95 percent.

EXAMPLE III

A dehydrogenation reaction was run as described in Example II on a cyclic dione feed solution containing 18.4 g of 3-hydroxy-2-cyclohexene-1-one (prepared as in Example I) in 267 g of butyl acetate. The dehydrogenation media consisted of 4 g of 5 weight percent palladium-on-carbon catalyst dispersed in 300 ml of butyl acetate. The cyclic dione feed rate was 60 ml/hr for a 5 hour reaction period, with the temperature and pressure, respectively, of the reaction mixture at about 180° C. and 52 p.s.i.g. Crude resorcinol was recovered in an amount of 18 g of better than 98 percent purity with a conversion of 98 percent based upon the cyclic dione.

EXAMPLE IV

A dehydrogenation reaction was run as described in Example II on a cyclic dione feed solution containing 18.8 g of 3-hydroxy-2-cyclohexene-1-one (prepared as in Example I) in 267 g of butyl acetate. The dehydrogenation media consisted of 4 g of 5 weight percent palladium-on-carbon catalyst dispersed in 300 ml of butyl acetate. The cyclic dione feed rate was 60 ml/hr for a 5 hour reaction period, with the temperature and pressure, respectively, of the reaction mixture at about 190° C. and 70 p.s.i.g. Crude resorcinol was recovered in an amount of 18.5 g of 97 percent purity with a conversion of 97 percent based upon the cyclic dione.

EXAMPLE V

A dehydrogenation reaction was run as described in Example II on a cyclic dione feed solution containing 110 g of 3-hydroxy-2-cyclohexene-1-one (prepared as in Example I) in 339 g of butyl acetate. The dehydrogenation media consisted of 4 g of 5 weight percent palladium-on-carbon catalyst dispersed in 300 ml of butyl acetate. The cyclic dione feed rate was 75 ml/hr for a 5 hour reaction period, with the temperature and pressure, respectively, of the reaction mixture at about 200° C. and 75 p.s.i.g. Crude resorcinol was recovered in an amount of 108 g of 95 percent purity with a conversion of 95 percent based upon the cyclic dione.

EXAMPLE VI

A dehydrogenation reaction was run as described in Example Ii on a cyclic dione feed solution containing 27 g of 3-hydroxy-2-cyclohexene-1-one (prepared as in Example I) in 262 g of water. The dehydrogenation media consisted of 5 g of 5 weight percent palladium-on-carbon catalyst dispersed in 300 ml of water. The cyclic dione feed rate was 40 ml/hr for a 6.5 hour reaction period, with the temperature and pressure, respectively, of the reaction mixture at about 170° C. and 145 p.s.i.g. Crude resorcinol was recovered in an amount of 26 g of 82 percent purity with a conversion of 80.4 percent based upon the cyclic dione.

EXAMPLE VII

A dehydrogenation reaction was run as described in Example II on a cyclic dione feed solution containing 12 g of 3-hydroxy-2-cyclohexene-1-one (DHR), prepared as in Example I, in 155 g of toluene heated to 80° C. to keep the DHR dissolved in the toluene. The dehydrogenation media consisted of 4 g of 5 weight percent palladium-on-carbon catalyst dispersed in 300 ml of toluene. The cyclic dione feed rate was 50 ml/hr until all of the feed was introduced to the reactor, with the temperature and pressure, respectively, of the reaction mixture at about 187° C. and 75 p.s.i.g. Crude resorcinol was recovered in an amount of 11.5 g of 90 percent purity with a conversion of 70 percent based upon the cyclic dione.

EXAMPLE VIII

A reactor tube as described in Example I was packed with 86 g of Filtrasorb No. 400 activated carbon to a catalyst bed volume of about 196 ml. A liquid mixture was prepared containing methyl 4-oxocaproate (MOC) and a two-component carrier consisting of n-hexane and toluene, in a mole ratio of MOC/n-hexane/toluene of 0.14/1.02/0.21. With the carbon bed at 380° C., the liquid mixture was pumped into the reactor tube so as to give a catalyst contact time of about 5.2 seconds. About 437 g of MOC was pumped into the reactor tube over a period of 22.5 hours. Condensate collected over the reaction period was heated at a temperature of 72° C. to provide a reflux condition. Methanol by-product of the cyclization reaction formed an azeotrope with the hexane; the azeotrope mixture was collected in a Dean-Stark trap. After methanol by-product was collected so that an azeotrope no longer formed, the reaction mixture was cooled under agitation. Then about 98 g of crystal product identified as 3-hydroxy-2-cyclohexene-1-one (DHR), was collected by filtering of the cooled reaction product, with the filtrate containing less than 0.5 weight percent DHR. Yield of DHR based on MOC fed to the reactor was 33 mole percent. This DHR product may be subjected to dehydrogenation as outlined in the foregoing examples to provide resorcinol.

Although specific examples of the instant invention have been set forth hereinabove, it is not intended that the invention be limited solely thereto, but is to include all the variations and modifications falling within the scope of the appended claims.

What is claimed is:

1. A process for making resorcinol or substituted resorcinols of the general formula

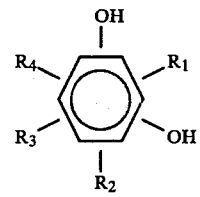

wherein $R_1$–$R_4$ are selected from hydrogen and alkyl groups of up to about 6 carbon atoms, with the proviso that the total number of carbon atoms of $R_1$–$R_4$ cannot exceed about 24, said process comprising the steps of:

(a) passing a vapor stream through a reaction zone containing a carbon catalyst suitable for catalyzing cyclization of a delta-keto ester to form a cyclic dione, said vapor stream comprising a delta-keto ester and a condensable non-reactive carrier, said delta-keto ester having the general formula

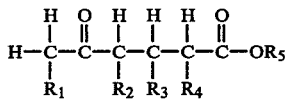

wherein $R_1$–$R_4$ are defined as before and $R_5$ is selected from alkyl, aryl and alkylaryl groups, with the proviso that the total number of carbon atoms of $R_5$ cannot exceed about 24 said non-reactive carrier having a sufficiently high boiling point so that said carrier is a liquid at 25° C. and one atmosphere pressure, whereby the vapor stream may be easily condensed and the cyclic dione subsequently separated from the carrier and from unreacted delta-keto ester;

(b) contacting a liquid solution containing cyclic dione obtained in step (a) with a supported noble metal catalyst at a pressure from about one atmosphere to about 20 atmospheres and at a temperature in a range from about 170° C. to about 250° C. for a time sufficient to dehydrogenate the cyclic dione and form resorcinol or a substituted resorcinol.

2. The process of claim wherein the carrier is selected from an organic acid, an aliphatic hydrocarbon and an aromatic hydrocarbon.

3. The process of claim 1 wherein the carrier is toluene.

4. The process of claim 1 wherein the liquid solution of step (b) comprises cyclic dione dissolved in a solvent, said solvent selected from the group consisting of aliphatic ethers, aliphatic alcohols, aliphatic esters, and water, provided that said selected solvent has a normal boiling point of less than about 170° C.

5. The process of claim 4 wherein said solvent is isopropyl alcohol.

6. The process of claim 4 wherein said solvent is butyl acetate.

7. The process of claim 1 wherein the liquid solution of step (b) comprises cyclic dione in an amount in a range from about 5 to about 25 percent by weight of the liquid solution.

8. The process of claim 1 wherein the supported noble metal catalyst comprises palladium or platinum on a carbon support.

9. The process of claim 8 wherein the noble metal is present in the catalyst in an amount in a range from about 0.5 to about 10 weight percent of the catalyst.

10. The process of claim 1 wherein said delta-keto ester is a 5-oxohexanoic acid ester.

11. The process of claim 1 wherein said delta-keto ester is methyl 4-oxocaproate.

12. A process for making resorcinol, the process comprising:

(a) passing a vapor stream in contact with an activated carbon cyclization catalyst the vapor stream comprising methyl 4-oxocaproate and an easily-condensable non-reactive carrier, the carrier characterized in being liquid at 25° C. and at one atmosphere pressure, to provide 3-hydroxy 2-cyclohexene-1-one as a cyclization product;

(b) condensing the vapor stream within a condensing zone having a temperature in a range from about 20° C. to about 50° C.;

(c) isolating the 3-hydroxy-2-cyclohexene-1-one from the condensed carrier;

(d) contacting a liquid solution containing 3-hydroxy-2-cyclohexene-1-one obtained in step (c) with a supported noble metal catalyst at a temperature in a range from about 170° C. to about 200° C. and under a pressure from about one atmosphere to about 20 atmospheres.

13. The process of claim 12 wherein the carrier is selected from the group consisting of an organic acid, an aliphatic hydrocarbon and an aromatic hydrocarbon.

14. The process of claim 12 wherein the carrier is a mixture of n-hexane and toluene.

15. The process of claim 12 wherein the liquid solution of step (d) comprises a solvent selected from aliphatic esters and aliphatic alcohols, provided that said selected solvent has a normal boiling point less than about 170° C.

16. The process of claim 12 wherein the liquid solution of step (d) comprises a solvent selected from the group consisting of butyl acetate and isopropyl alcohol.

17. The process of claim 12 wherein the supported nobel metal catalyst is a palladium-on-carbon catalyst having palladium in an amount in a range from about 0.5 to about 10 weight percent of the catalyst.

* * * * *